United States Patent
Brighton et al.

(10) Patent No.: US 7,158,835 B2
(45) Date of Patent: Jan. 2, 2007

(54) DEVICE FOR TREATING OSTEOPOROSIS, HIP AND SPINE FRACTURES AND FUSIONS WITH ELECTRIC FIELDS

(75) Inventors: Carl T. Brighton, Malvern, PA (US); Solomon R. Pollack, Wales, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 130 days.

(21) Appl. No.: 10/499,191

(22) PCT Filed: Jul. 10, 2002

(86) PCT No.: PCT/US02/21881

§ 371 (c)(1),
(2), (4) Date: Jun. 17, 2004

(87) PCT Pub. No.: WO03/057312

PCT Pub. Date: Jul. 17, 2003

(65) Prior Publication Data

US 2005/0228462 A1    Oct. 13, 2005

Related U.S. Application Data

(60) Provisional application No. 60/342,450, filed on Dec. 21, 2001.

(51) Int. Cl.
*A61N 1/40* (2006.01)

(52) U.S. Cl. .......................................... 607/51; 607/43

(58) Field of Classification Search ................. 607/50, 607/51, 43, 117, 118; 600/13–15
See application file for complete search history.

(56) References Cited

U.S. PATENT DOCUMENTS

| | | | |
|---|---|---|---|
| 4,430,999 A | 2/1984 | Brighton et al. | 128/419 |
| 4,442,846 A | 4/1984 | Brighton et al. | 128/784 |
| 4,467,808 A | 8/1984 | Brighton et al. | 128/419 F |
| 4,487,834 A | 12/1984 | Brighton | 435/173 |
| 4,506,674 A | 3/1985 | Brighton et al. | 128/419 |
| 4,509,520 A | 4/1985 | Dugot | 128/419 |
| 4,535,775 A | 8/1985 | Brighton et al. | 128/419 F |
| 4,549,547 A | 10/1985 | Brighton et al. | 128/419 F |
| 4,600,010 A | 7/1986 | Dugot | 128/419 |
| 4,998,532 A * | 3/1991 | Griffith | 607/2 |
| 5,014,699 A | 5/1991 | Pollack et al. | 128/419 |
| 5,038,797 A | 8/1991 | Batters | 128/798 |

(Continued)

FOREIGN PATENT DOCUMENTS

WO    WO 01/62336 A1    8/2001

(Continued)

OTHER PUBLICATIONS

Brighton, C.T., et al., "Signal transduction in electrically stimulated bone cells," *J. Bone Joint Surg. Am.*, 2001, 83-A(10), 1514-1523.

(Continued)

*Primary Examiner*—Jeffrey R. Jastrzab
(74) *Attorney, Agent, or Firm*—Woodcock Washburn, LLP (57) ABSTRACT

A technique and device for preventing and/or treating osteoporosis, hip and spine fractures, and/or spine fusions by incorporating at least one conductive coil (110) into a garment (90) adapted to be worn adjacent to the patient's skin over a treatment area and applying an electrical signal to the coil effective to produce a magnetic flux the penetrates the treatment area so as to produce an electric field in the bones and the treatment area.

25 Claims, 10 Drawing Sheets

U.S. PATENT DOCUMENTS

| | | | |
|---|---|---|---|
| 5,269,746 A | 12/1993 | Jacobson | 600/13 |
| 5,273,033 A | 12/1993 | Hoffman | 607/46 |
| 5,338,286 A | 8/1994 | Abbott et al. | 600/14 |
| 5,374,283 A | 12/1994 | Flick | 607/46 |
| 5,743,844 A | 4/1998 | Tepper et al. | 600/14 |
| 5,792,209 A * | 8/1998 | Varner | 607/51 |
| 5,882,292 A * | 3/1999 | Miyaguchi | 600/9 |
| 6,083,149 A | 7/2000 | Wascher et al. | 600/9 |
| 6,132,362 A | 10/2000 | Tepper et al. | 600/14 |
| 6,186,940 B1 | 2/2001 | Kirschbaum | 600/12 |
| 6,261,221 B1 | 7/2001 | Tepper et al. | 600/14 |
| 6,560,487 B1 * | 5/2003 | McGraw et al. | 607/51 |
| 2002/0052634 A1 | 5/2002 | March | 607/50 |
| 2003/0211084 A1 | 11/2003 | Brighton et al. | 424/93.7 |

FOREIGN PATENT DOCUMENTS

WO    WO 2005/070136 A2    8/2005

OTHER PUBLICATIONS

Pienkowski, D., et al., "Low-power electromagnetic stimulation of osteotomized rabbit fibuiae," *J. of Bone & Joint Surgery*, 1994, 76-A(4), 489-501.

Wang, W., et al., "Up-regulation of chondrocyte matrix genes and products by electric fields," *Clin. Orthopaedics & Related Res.*, 2004, 427S, S163-S173.

Aaron, R.K., et al., "The conservative treatment of osteonecrosis of the femoral head," *Clin. Orthop.*, 1989, 249, 209-218.

Aaron, R.K., et al., "Stimulation of experimental endochondral ossification by low-energy pulsing electromagnetic fields," *J. Bone Miner. Res.*, Nov. 2, 1989, 4, 227-233.

Bassett,C.A.L., "Low energy pulsing electromagnetic fields modify biomedical processes," *BioEssays*, 1987, 6(1), 36-42.

Bassett, C.A.L., et al., "Effects of pulsed electromagnetic fields on Steinberg ratings of femoral head osteonecrosis," *Clin. Orthop.*, Sep. 1989, 246, 172-185.

Bassett, C.A.L., et al., "Fundamental and practical aspects of therapeutic uses of pulsed electromagnetic fields (PEMSs)," *Crit. Rev. Biomed. Eng.*, 1989, 17(5), 451-529.

Bassett, C.A.L., et al., "Pulsing electromagnetic field treatment in ununited fractures and failed arthrodeses," *JAMA*, Feb. 5, 1982, 247(5), 623-628.

Binder, A., et al., "Pulsed electromagnetic field therapy of persistent rotator cuff tendonitis," *Lancet*, Mar. 31, 1984, 695-698.

Brighton, C.T., et al., "A multicenter study of the treatment of non-union with constant direct current," *J. Bone and Joint Surgery*, Jan. 1981, 63-A(1), 2-13.

Brighton, C.T., et al., "Treatment of recalcitrant non-union with a capacitively coupled electrical field," *J. Bone and Joint Surgery*, Apr. 1985, 67-A(4), 577-585.

Brighton, C.T., et al., "Treatment of castration-induced osteoporosis by a capacitively coupled electrical signal in rat vertebrae," *J. Bone and Joint Surgery*, Feb. 1989, 71-A(2), 228-236.

Brighton, C.T., et al., "Increased cAMP production after short-term capacitively coupled stimulation in bovine growth plate chondrocytes," *J. Orthop. Res.*, 1988, 6, 552-558.

Brighton, C.T., et al., "Treatment of denervation/disuse osteoporosis in the rat with a capacitively coupled electrical signal: effects on bone formation and bone resorption," *J. Orthop. Res.*, 1988, 6, 676-684.

Brighton, C.T., et al., "Fracture healing in the rabbit fibula when subjected to various capacitively coupled electrical fields," *J. Orthop. Res.*, 1985, 3, 331-340.

Brighton, C.T., et al., "*In vitro* bone-cell response to a capacitively coupled electrical field," *Clin. Orthop. Related Res.*, Dec. 1992, 285, 255-262.

Brighton, C.T., et al., "Prevention and treatment of sciatic denervation disuse osteoporosis in rat tibia with capacitively coupled electrical stimulation," *Bone*, 1985, 6, 87-97.

Brighton, C.T., et al., "Treatment of nonunion of the tibia with a capacitively coupled electrical field," *J. of Trauma*, 1984, 24(2), 153-155.

Brighton, C.T., et al., "Tibial nonunion treated with direct current, capacitive coupling, or bone graft," *Clin. of Orthop. and Related Res.*, 1995, 321, 223-234.

Carter, E.L., et al., "Field distributions in vertebral bodies of the rat during electrical stimulation: a parametric study," *IEEE Trans. on Biomed. Eng.*, Mar. 1989, 36(3), 333-345.

Goodwin, C.B., et al., "A double-blind study of capacitively coupled electrical stimulation as an adjunct to lumbar spinal fusions," *Spine*, 1999, 24(13), 1349-1356.

Grodzinky, A.J., "Electromechanical and physicochemical properties of connective tissue," *Crit. Rev. Biomed. Engng.*, 1983, 9(2), 133-199.

Harrison, M.H.M., et al., "Use of pulsed electromagnetic fields in perthes disease: report of a pilot study," *J. Pediatr. Orthop.*, 1984, 4, 579-584.

Jones, D.B., et al., "PEMF effects on differentiation and division in mirine melanoma cells are mediated indirectly through cAMP," *Trans. BRAGS 6*, 1986, 51.

Lorich, D.G., et al., "Biochemical pathway mediating the response of bone cells to capacitive coupling," *Clin. Orthop. and Related Res.*, 1998, 350, 246-256.

Massardo, L., et al., "Osteoarthritis of the knee joint: an eight year prospective study," *Ann Rheum Dis.*, 1989, 48, 893-897.

Mooney, V., "A randomized double-blind prospective study of the efficacy of pulsed electromagnetic fields for inter body lumbar fusions," *Spine*, 1990, 15(7), 708-712.

Norton, L.A., et al., "Pulsed electromagnetic fields alter phenotypic expression in chondroblasts in tissue culture," *J. of Orthop. Res.*, 1988, 6, 685-689.

Rodan, G.A., et al., "DNA synthesis in cartilage cells is stimulated by oscillating electric fields," *Science*, Feb. 10, 1978, 199, 690-692.

Ryaby, J.T., et al., "Pulsing electromagnetic fields affect the phosphorylation and expression of oncogene proteins," *Trans. BRAGS 6*, 1986, p. 78.

Ryaby, J.T., et al., "The effect of electromagnetic fields on protein phosphorylation and synthesis in murine melanoma cells," *BRAGS*, p. 32.

Wang, W., et al., "The increased level of PDGF-A constributes to the increased proliferation induced by mechanical stimulation in osteoblastic cells," *Biochem. And Molecular Biol. International*, Oct. 1997, 43(2), 339-346.

Zhuang, H., et al., "Mechanical strain-induced proliferation of osteoblastic cells parallels increased TGF-$\beta$1 mRNA,"*Biochem. Biophys. Res. Commun.*, 1996, 229, 449-453.

Zhuang, H., et al., "Electrical stimulation induces the level of TGF-$\beta$1 mRNA in osteoblastic cells by a mechanism involving calcium/calmodulin pathway," *Biochem. Biophys. Res. Commun.*, 1997, 237, 225-229.

U.S. Appl. No. 60/302,846, filed Jul. 3, 2001, Pollack et al.

* cited by examiner

DEVICE FOR TREATING OSTEOPOROSIS, HIP AND SPINE FRACTURES AND FUSIONS WITH ELECTRIC FIELDS

CROSS-REFERENCE TO RELATED APPLICATIONS

This application is the National Stage of International Application No. PCT/US02/21881, filed Jul. 10, 2002, which claims the benefit of U.S. Provisional Application No. 60/342,450, filed Dec. 21, 2001, the disclosure of which is incorporated herein by reference in its entirety.

BACKGROUND OF THE INVENTION

1. Field of the Invention

The present invention relates to a device and method for the prevention and/or treatment of osteoporosis, fractures of the hip, spine fractures, and/or spine fusions using inductively coupled electric fields generated by coils inserted into a patient's undergarments and powered by a portable power source.

2. Description of the Prior Art

As previously reported in U.S. Pat. No. 4,467,808, issued Aug. 28, 1984, and as reported in three published papers by Brighton et al (*Bone*, 6:87–97, 1985; *J. Orthopaedic Research*, 6:676–684, 1988; and *J. Bone and Joint Surger*, 71A: 228–236, 1989) an appropriate capacitively coupled electric field prevented and/or reversed osteoporosis induced in the rat vertebra or tibia. It has also been previously reported in U.S. Pat. No. 4,535,775, issued Aug. 20, 1985, and in several published papers by Brighton et al (*J. Trauma*, 24:153–155, 1984; *J. Orthopaedic Research*, 3:331–340, 1985; and *J. Bone and Joint Surgery*, 67A: 577–585, 1985) that an appropriate capacitively coupled electric field increased the rate of healing in fresh fractures in the rabbit fibula and healed human fracture nonunions at a rate comparable to that of bone graft surgery (*Clin. Orthop. And Related Research*, 321: 223–234, 1995). Lastly, it was reported recently that an appropriate capacitively coupled electric field used as an adjunct to lumbar spinal fusion significantly increased the rate of fusion when compared to patients who had spinal fusion without electrical stimulation (Goodwin, Brighton, et al, *Spine*, 24:1349–1356, 1999).

All of the above studies used capacitive coupling, a method of noninvasively producing an electric field in tissues within the body such as bone and cartilage. Capacitive coupling, as used in those studies, requires the use of a pair of electrodes attached to the surface of the patient's skin adjacent to or near the location of treatment. Capacitive coupling is a very convenient, patient "friendly" method of applying electricity to the patient in the treatment of bone fractures, nonunions, bone defects, and localized lumbar spine fusions. However, capacitive coupling is not a practical way of treating multiple segment spine fusions or to treat a relative large area. This limitation of capacitive coupling led the present inventors to invent a method and device for achieving the same internal electrical fields in vertebrae at multiple levels by using either multiple electrode pairs or by using strip electrodes, as described in U.S. Provisional Patent Application No. 60/302,846. The multiple electrode pairs or strip electrodes (one long electrode on either side of the spine) described therein are designed to be worn 24 hours per day and to be changed periodically for a treatment period of, e.g., 8–12 weeks.

The present inventors also set out to extend the techniques described in the above-mentioned patents and articles to the treatment of osteoporosis, fractures of the hip or spine, and/or spine fusions in humans. However, the present inventors soon discovered that transferring existing data to the application of electric signals to the human spine and hips in patients with osteoporosis, fractures of the hip or spine, and/or spine fusions was far from straightforward. A determination of the proper electric field amplitude and method of applying electricity to the patient for the treatment of osteoporosis, fractures of the hip or spine, and/or spine fusions needed to be developed. Capacitive coupling was substantially eliminated as a method of producing an electric field in the spine to treat osteoporosis because family assistance is required to apply the electrodes. Such assistance is frequently unavailable in this generally older patient population afflicted with osteoporosis and hip and spine injuries. Moreover, such patients typically will require the application of electric fields for months to years and possibly for the duration of the patient's life.

Accordingly, it is desired to develop an equivalent electric field in vertebrae and other bones and tissues, such as the hip, as achieved with capacitive coupling, except that it is desired to use only electromagnetic fields instead of capacitively coupled fields so that electrodes will not need to be applied to the patient. Inductive coupling devices will create the opportunity for the development of garments and the like that can be readily applied to the treatment area by the patient. The present invention addresses the features of such garments.

SUMMARY OF THE INVENTION

The present invention addresses the above-mentioned needs in the art by incorporating flexible coils made of wire or conductive thread into a patient's undergarment. A time varying electric field as described herein is produced in the coils by applying electrical signals from a portable power supply worn by the patient. The time varying electric field in the coils produces a time varying magnetic field that readily penetrates into the tissue beneath the coil, and which, in turn, produces a time varying electric field in such tissues. In embodiments described herein, the tissues include the vertebra and the bones of the hip that are treated to prevent or minimize the spread of osteoporosis, to heal and/or prevent fractures of the hip or spine, and/or to treat spine fusion.

The present invention relates to a device and method of preventing and/or treating osteoporosis, fractures of the hip, spine fractures and/or spine fusions in a patient by incorporating at least one conductive coil into a garment adapted to be worn adjacent the patient's skin, whereby the garment, when worn, causes the coil to be located over a treatment area of the patient, and applying an electrical signal to the coil effective to produce a magnetic flux that penetrates the treatment area so as to produce an electric field in the bones and tissues of the treatment area effective to treat osteoporosis, fractures, or fusion of the bones of the treatment area. Preferably, a portable power device creates the electrical signal for application to the coil and is sufficiently small and light to be carried on the patient's body when the garment is being worn. The portable power device is adapted to provide a 60 kHz sinusoidal electrical current with a sine wave amplitude of 100 mA to the coil in the representative embodiments, although other types of electric signals may also be applied to provide suitable treatments.

In a first embodiment, the garment is an undershirt and the coil is configured in a racetrack design having a long axis along the treatment area of the patient's spine when incorporated into the undershirt. The coil may be woven into the undershirt, placed in a pouch in the undershirt, or attached to the undershirt by VELCRO®.

In a second embodiment, the garment is underpants and the coil is circular in shape and centered over the patient's hip when incorporated into the underpants. The coil may be woven into the underpants, placed in a pouch in the underpants, or attached to the underpants by VELCRO®. The underpants may accept a circular-shaped coil over one or both hips of the patient.

BRIEF DESCRIPTION OF THE DRAWINGS

A system and method for prevention and treatment of osteoporosis, hip or spine fractures, and/or spine fusion with electric fields in accordance with the invention is further described below with reference to the accompanying drawings, in which.

DETAILED DESCRIPTION OF THE INVENTION

Device Geometry

Instead of self-adhering electrodes being attached to the surface of the patient's skin and receiving an electrical signal for generating a time varying electromagnetic field in the tissue beneath the electrodes as in the case of prior art capacitive coupling systems, the present invention utilizes flexible coils made of wire or conductive thread that are incorporated into a garment to be worn for about eight hours per day. A time varying electric field is produced in the coils from a small, portable power supply worn by the patient that produces a time varying electromagnetic field that readily penetrates into the tissue beneath the coil, which, in turn, produces a time varying electric field in such tissues. In the exemplary embodiments described herein, such tissues include the vertebra and the bones of the hip. The problem of determining how to produce an equivalent electromagnetic field as in the case of capacitive coupling requires an analysis of the time varying currents to be applied to the appropriately designed coils of conducting material.

Figure 1A:
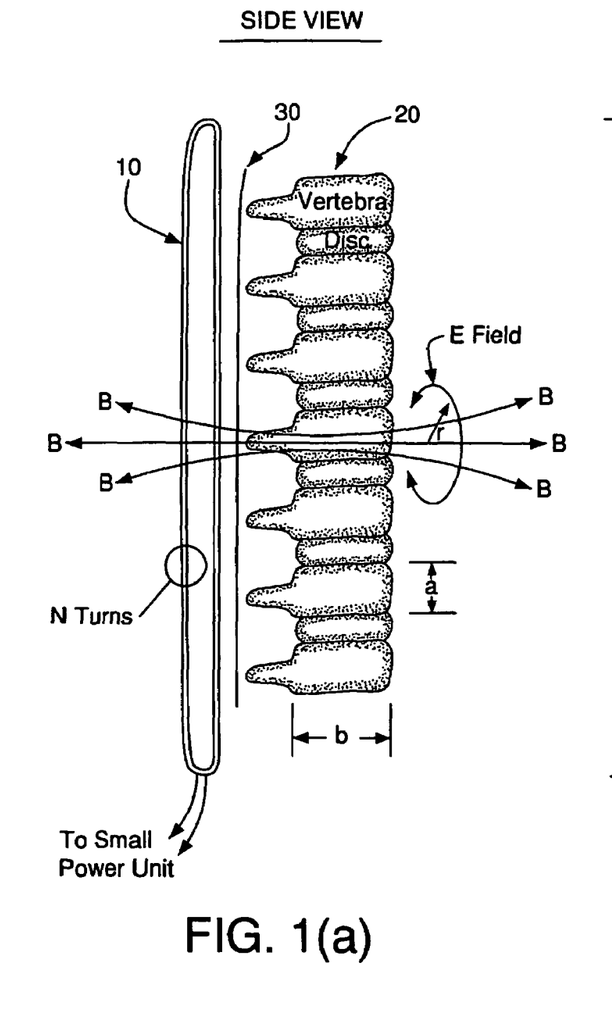
FIGS. 1(a) and 1(b) illustrates side and front views, respectively, of N-turns of a coil of wire made in the shape of a racetrack and incorporated into a garment worn by the patient so that the coil is placed over a treatment area of the patient's spine.
Figure 1B:
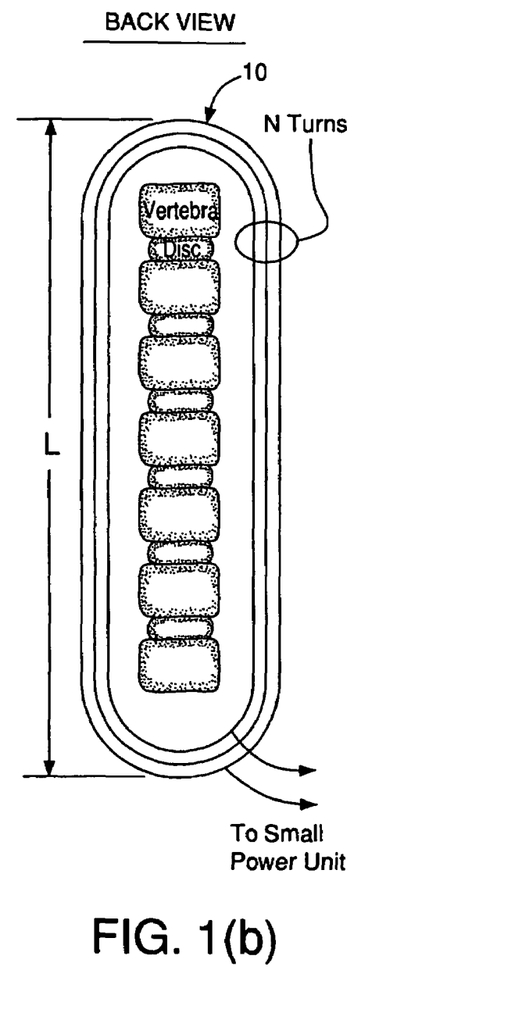

FIGS. 1(a) and 1(b) together show N-turns of a coil 10 preferably made of insulated copper wire or other suitable conductor in the shape of a "race track". In accordance with a first embodiment of the invention, coil 10 is incorporated into a garment (not shown) and worn by a patient so that the coil 10 is placed over a treatment area of the patient's spine 20. A time varying current in the coils, produced by a power unit (not shown), in turn produces the magnetic flux, B, which readily penetrates the patient's skin 30 to the tissues of the spine 20. This flux B in turn produces the transverse electric field, E, in the bones of the spine 20 and results in effective treatment of osteoporosis and bone fusion, repair or growth. In FIG. 1, "a" represents the mean vertebral length, "b" represents the mean vertebral diameter, "L" represents the length of coil 10 for incorporation into a garment designed to treat "n" vertebrae, and "r" is the distance of application of the transverse electric field, E.

Figures 2A, 2B:
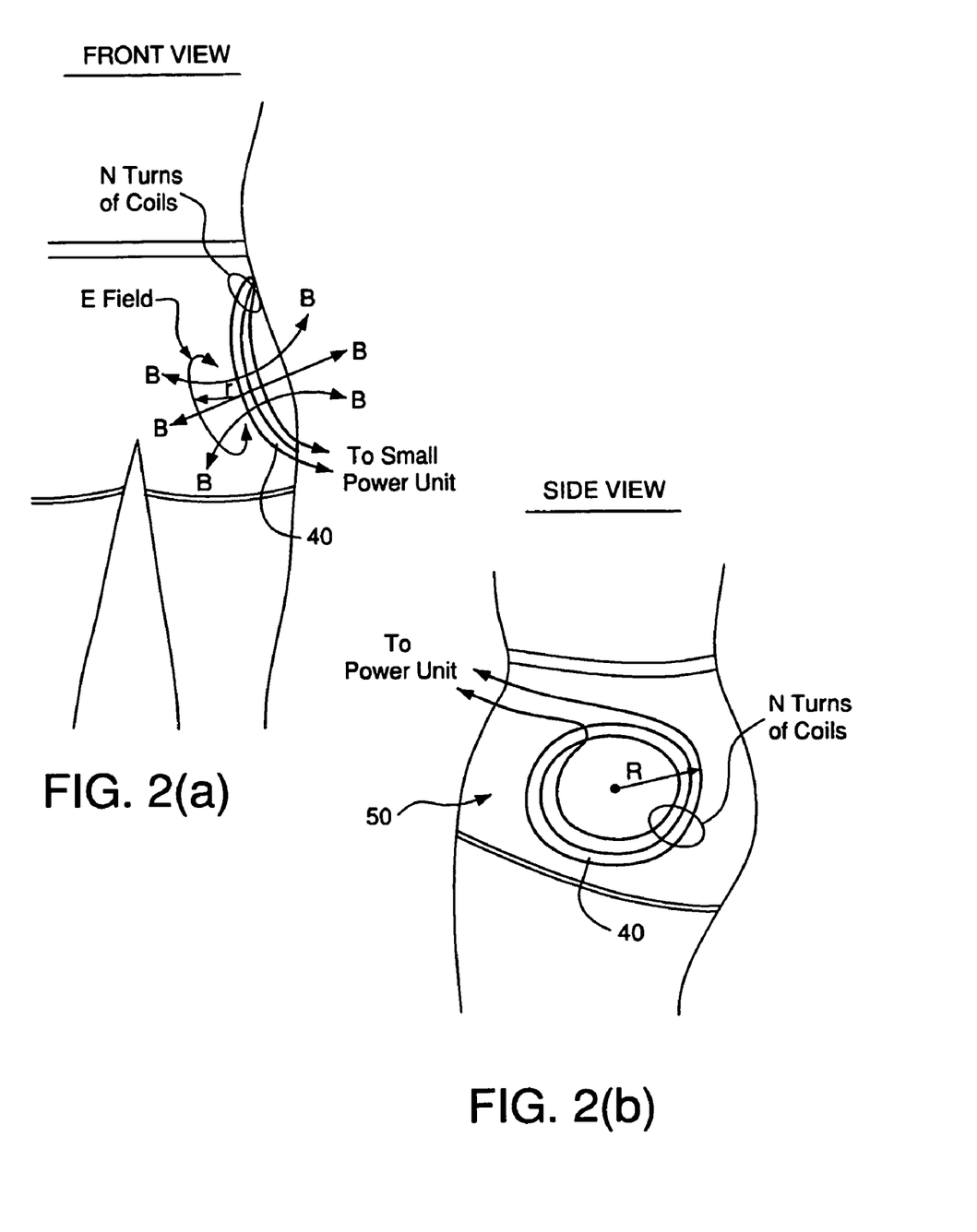
FIGS. 2(a) and 2(b) illustrate front and side views, respectively, of N-turns of a coil of wire in a circular configuration and incorporated into a garment worn by the patient so that the coil is placed over a treatment area of one of the patient's hips. Two coils could be used to treat both hips simultaneously.

FIGS. 2(a) and 2(b) together show N turns of coil 40 of radius R preferably made of insulated copper wire or other suitable conductor in the shape of a circle. In accordance with a second embodiment of the invention, coil 40 is incorporated into a garment 50 and worn by a patient so that the coil 40 is placed over the treatment area of the hip of the patient. The power unit (not shown) produces a time varying current to the coil 40 on the hip resulting in the flux, B, and, in turn, the transverse electric field, E, in the tissues, which field E causes the repair/growth process in the bones of the hip.

In both embodiments, the power unit is preferably small, light in weight, and carried in a pouch somewhere on the patient.

Current in Coil Required to Generate Therapeutic Electric Field

In this section, the values of the current in the coil 10 or the coil 40 and the frequency of such current are calculated that will generate an electric field in the range of amplitude and frequency with a proven therapeutic value for the treatment of osteoporosis, hip or bone fractures, spine fusions, and the like. For the geometry shown in FIG. 3 (the same geometry as for the hip coil 40 in FIG. 2), the transverse electric field amplitude, /E/, is related to the time varying magnetic flux B by Equation 1:

$$/E/ = \frac{\partial B \cdot r}{\partial t \cdot 2} \tag{1}$$

where /E/ is the magnitude of E shown in FIGS. 1 and 2, $$\frac{\partial B}{\partial t}$$

is the partial derivative of the magnetic flux, B, shown in FIGS. 1 and 2 with respect to time, and r is the distance as shown in FIGS. 1 and 2.

In accordance with the invention, there are at least two possible coil configurations that can be used. In the case of the hip coil 40, a circular coil would facilitate anatomical compliance, while for the spine coil 10, a "race track" configuration designed to fit over the spine 20 would be desirable. Although those skilled in the art will appreciate that alternative configurations are possible, the electric field amplitude will be calculated for the two presently preferred configurations shown in FIGS. 1 and 2. The electric field amplitude for these two cases will be calculated for the central regions of the coil areas. Those skilled in the art will appreciate that the electric field amplitude will vary with position as is the case with capacitive coupling when electrodes are used. This assures that the therapeutic range of the E field is present if the central value is matched to the central value or mean value from capacitive coupling.

Case #1 Circular Coil of N-Turns (FIG. 2)

Figure 3:
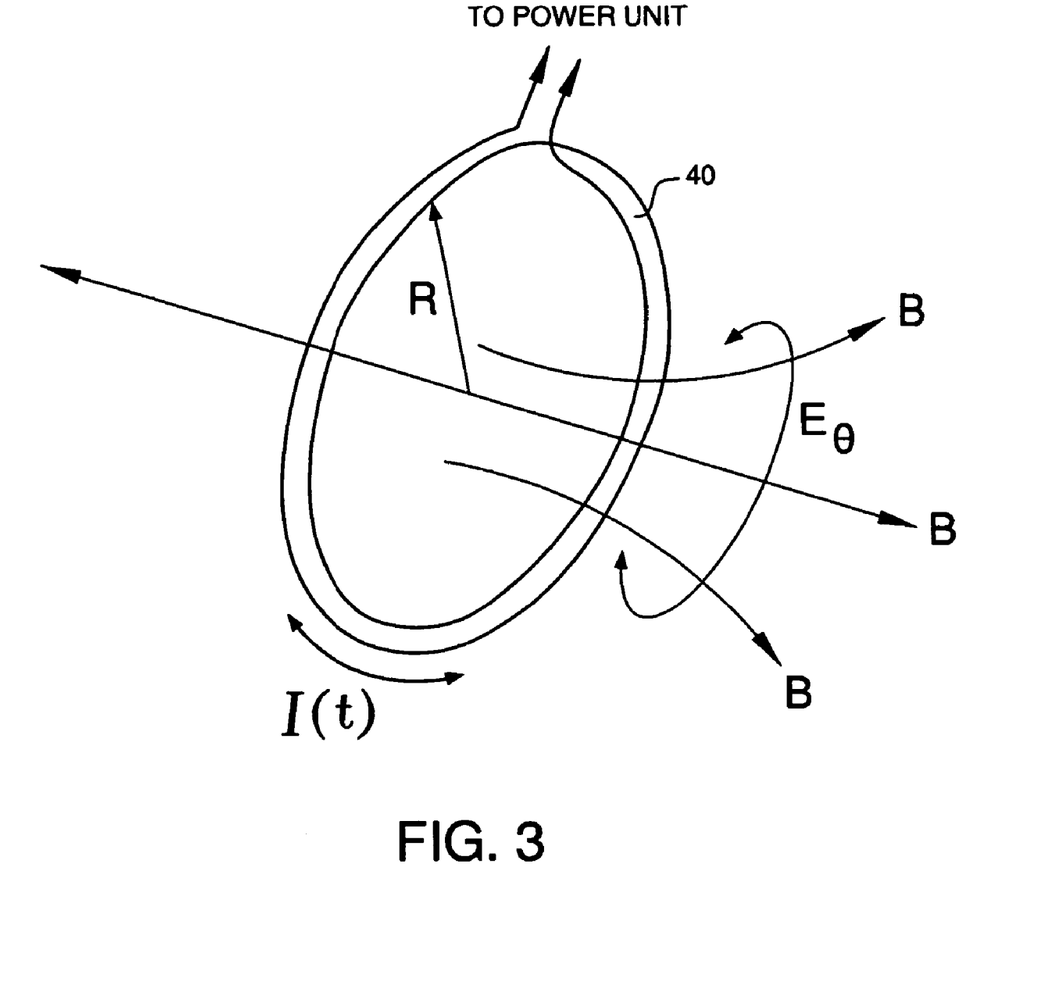
FIG. 3 illustrates the geometry of the coil of FIG. 2.
Figure 4:
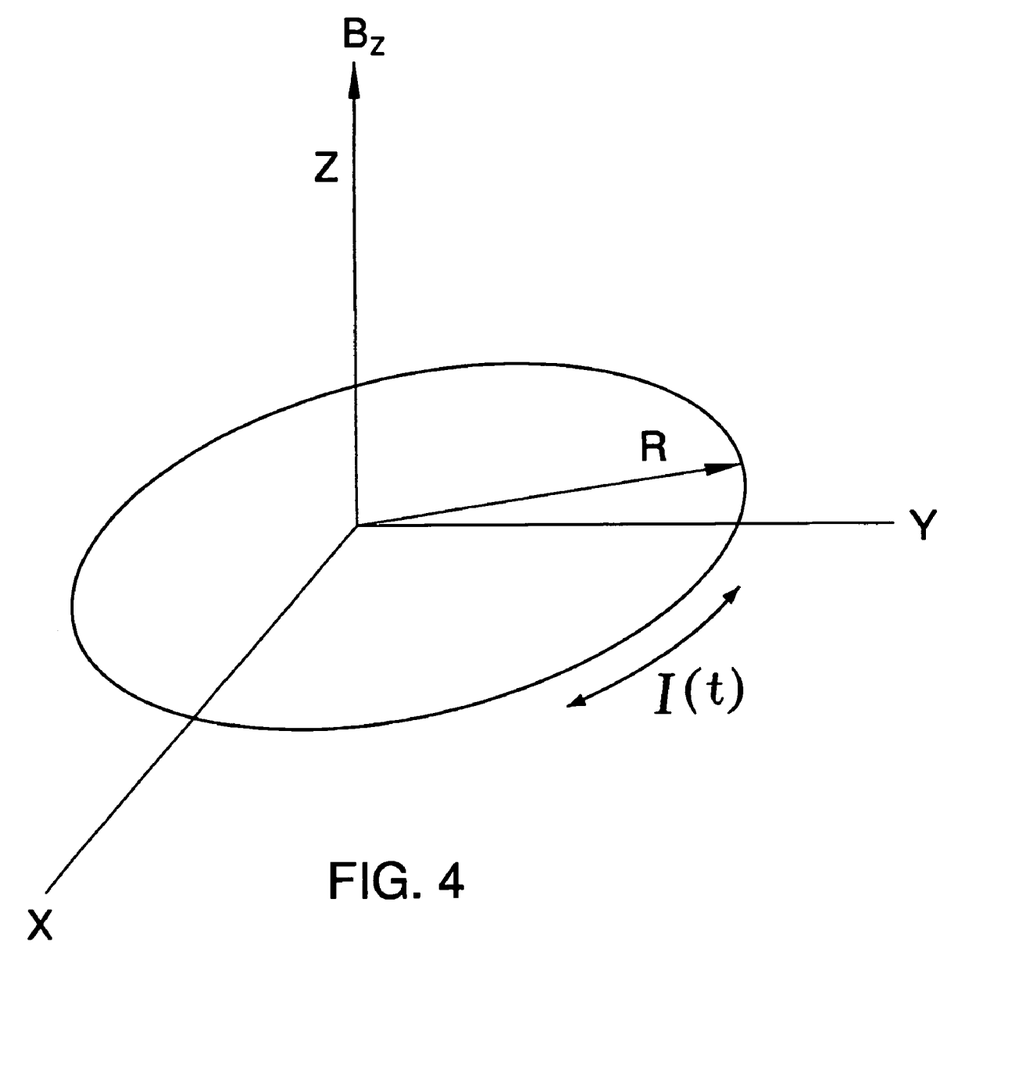
FIG. 4 illustrates the magnetic flux Bz generated by the coil of FIG. 2.

As shown in FIG. 3, hip coil 40 has a coil radius of R and a coil current of I(t). The magnetic flux, in the central region of the coil and perpendicular to the plane of the coil $B_z$, as shown in FIG. 4, is given by the equation:

$$B_z = \frac{\mu o \cdot I \cdot N \cdot R^2}{2[(R)^2 + z^2]^{3/2}}$$

where $\mu_o$ is the magnetic permeability of free space (and human tissue) and N is the number of turns of the coil. If the hip bones are located in the region where r<<R and at a distance z=R, then the approximate value of $B_z$ is given by Equation 2:

$$B_z = \frac{N \cdot \mu o \cdot I}{4 \cdot \sqrt{2} R} \quad (2)$$

Using Equations (1) and (2) together results in Equation 3:

$$|E| = \frac{\mu o \cdot N \cdot r}{8 \cdot \sqrt{2} R} \frac{\partial I}{\partial t} \quad (3)$$

where $$\frac{\partial I}{\partial t}$$

is the partial derivative of the coil current I(t) with respect to time. The time dependence of the current is chosen to be sinusoidal and of a frequency of 60 kHz in order to match the successful time dependence of capacitive coupling. Accordingly, I is given by Equation 4:

$$I = I_0 e^{iwt} \quad (4)$$

where $I_0$ is the sine wave amplitude and $w=2\pi f$ where f is the frequency equal to 60 kHz. Then, substituting Equation 4 in Equation 3 gives Equations 5 and 6:

$$|E_0| = \frac{\mu o \cdot N \cdot I_0 \cdot w \cdot r}{8\sqrt{2} R} \quad (5)$$

-continued $$|E_0| = \frac{\mu o \cdot N \cdot I_0 \cdot f r \pi}{4\sqrt{2} R} \quad (6)$$

where $|E_0|$ is the electric field amplitude. For the case where $f=6\times10^4$ Hz, and for $\mu o=1.26\times10^{-6}$ Hz/m, $r = 2$ cm $=2\times10^{-2}$ m, and $\pi=3.14$, then Equation 6 reduces Equation 7:

$$|E_0| = 0.84 \times 10^{-3} \frac{N \cdot I_0}{R} \quad (7)$$

For example, for a coil having the following parameters, the electric field amplitude value $|E_0|$ would be 22.4 mV/cm or 2.24 V/m:

R=7.5 cm=7.5×10$^{-2}$ m;

N=2000 Turns=2×10$^3$ $I_0$=100 mA

Those skilled in the art will appreciate that a greater number of turns of the coil and/or a higher current in the coil can increase these values for the electric field amplitude. Also, the use of magnetic material inside of the coil can increase the flux density, B, and therefore the value of $|E|$. In addition, square pulsed current with high 60 kHz harmonics can also be used to increase the signal strength.

Case #2: The "Race Track" Coil of N Turns (FIG. 1)

In the case of the spine coil 10 of FIG. 1, it is assumed that the total length L of the coil is much greater than twice the diameter b of a vertebra. The magnetic flux B at the center of the racetrack coil 10 is then approximately given by Equation 8:

$$B = 2 \cdot \frac{\mu o \cdot I \cdot 2L}{4\pi \cdot b(L^2 - b^2)^{1/2}}, \quad (8)$$

where I is the current in the racetrack coil 10 and b and L are as shown in FIG. 1. If L>>b, then Equation 8 becomes Equation 9:

$$B = \frac{\mu o \cdot I}{\pi b} \quad (9)$$

Utilizing Equation (9) in Equation (1) gives Equation 10:

$$E = \frac{\mu o \cdot r}{\pi \cdot b \cdot 2} \cdot \frac{\partial I}{\partial t}. \quad (10)$$

If $I = N \cdot I_0 \cdot e^{iwt}$, a sine wave at 60 kHz with N turns, then:

$$|E_0| = \mu o \frac{r}{b} N \cdot f \cdot I o \quad (11)$$

Taking r=a and a=b (from FIG. 1), then:

$$|E_0| = \mu o \cdot N \cdot f \cdot I_0 \quad (12)$$

If $\mu o = 1.26 \cdot 10^{-6}$ Hz/m, then $/E_O/=2.26$ V/m$=22.6$ mV/cm if:

$$N = 300 \text{ turns}$$

$$f = 60 \text{ kHz} = 6 \cdot 10^4 \frac{1}{\text{sec}}$$

and $$I_0 = 100 \text{ mA.}$$

Power Device Design

The power unit is light (approximately 8 ounces), and small (approximately the size of a cigarette pack), and runs on a rechargeable battery pack.

In the case of the hip, the power unit has resistors/transistors (or circuit chip) so designed to deliver a 60 kHz, sinusoidal electrical current with a sine wave amplitude of 100 mA to a coil of 2000 turns of conductive material. This produces an internal electric field in the hip of 22.4 mV/cm.

In the case of the spine, the same power unit design delivers a 60 kHz sinusoidal electrical current with a sine wave amplitude of 100 mA to a coil with 300 turns of conductive material. This produces an internal electric field in the vertebrae of 22.6 mV/cm.

Additional features of this power supply may include physician read out, compliance monitoring, stabilization circuitry, and other capabilities consistent with state of the art electronics.

Garment Design:

The garment for the spine looks like an undershirt that has the conductive, flexible coil 10 either woven into the garment over the appropriate area of the spine 20 or the coil 10 may slip into a pouch in the undershirt at the appropriate level. On the other hand, the coil 10 may be attached to VELCRO® strips at the desired location.

Figure 5A:
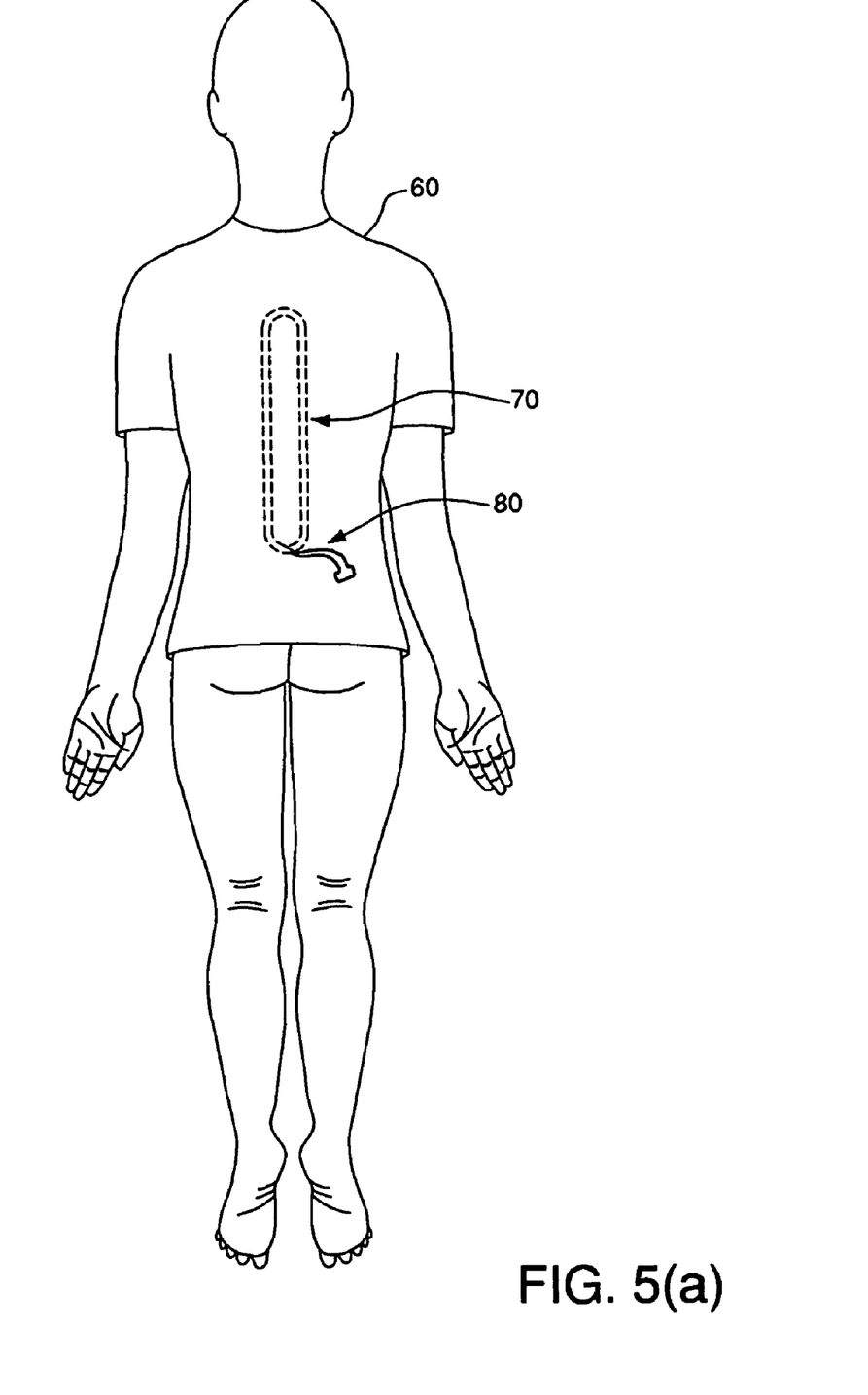
FIG. 5(a) illustrates an undershirt modified to include the conductive flexible coil of FIG. 1 woven into the undershirt for placement over the treatment area of the patient's spine.

FIG. 5(a) illustrates an undershirt 60 modified to include a flexible conductive coil 70 of the type shown in FIG. 1 woven into the undershirt 60 for placement and retention at a location centered over the treatment area of the patient's spine. A connector 80 with soft, flexible leads connects the coil 70 to a power pack (not shown) preferably worn on a belt around the patient's waist or in a pouch of the undershirt 60.

Figure 5B:
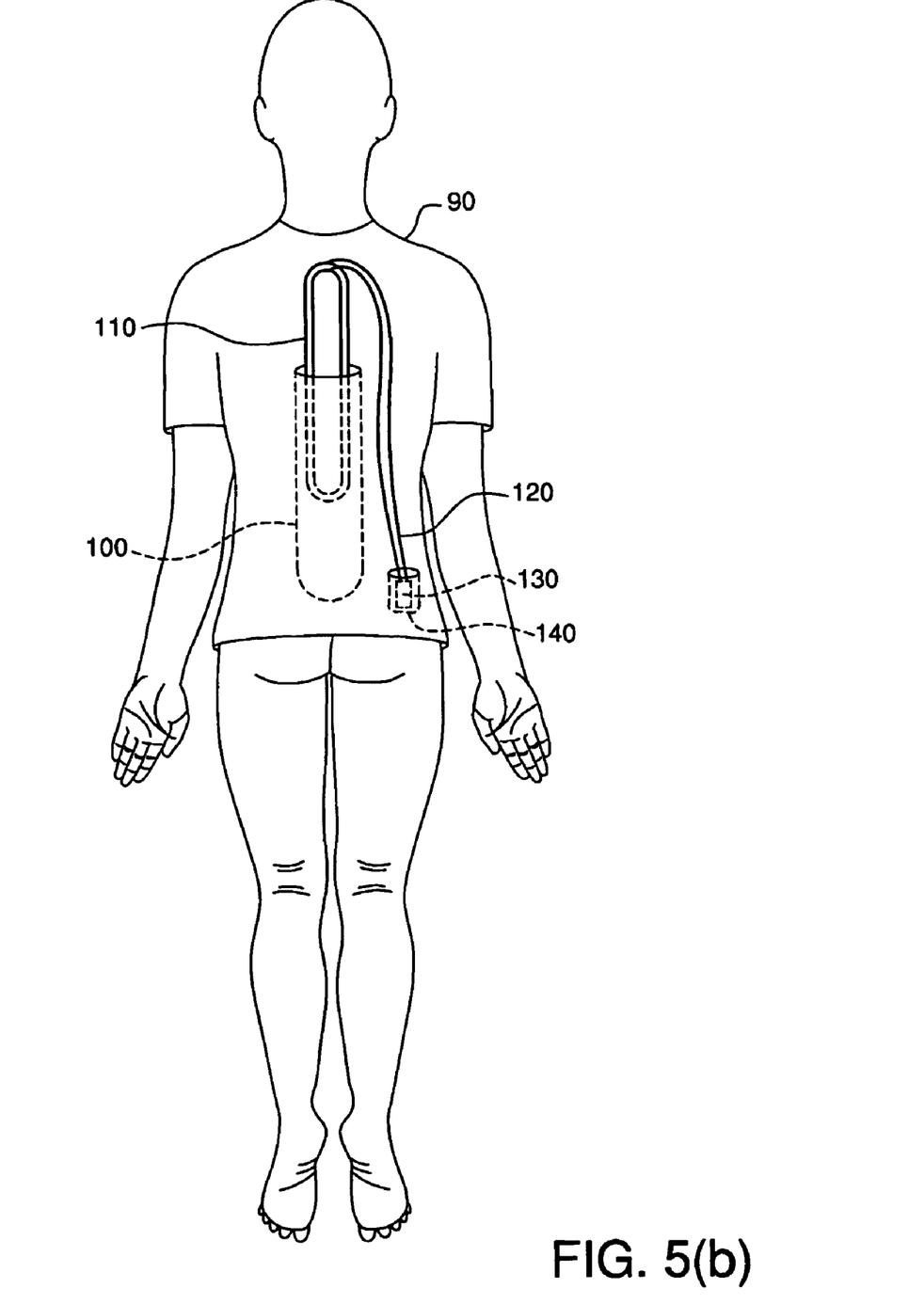
FIG. 5(b) illustrates an undershirt modified to include a pouch for receiving the conductive flexible coil of FIG. 1 for placement over the treatment area of the patient's spine.

FIG. 5(b) illustrates an undershirt 90 modified to include a pouch 100 for receiving the conductive flexible coil 110 of the type shown in FIG. 1 except that the coil 110 is mounted on a substrate or fabric to facilitate insertion into the pouch 100. The pouch 100 is centered over the treatment area of the patient's spine. A connector 120 connects the coil 110 to power pack 130 that is preferably worn on a belt around the patient's waist or placed in a pouch 140 of the undershirt 90 as shown. The pouches may be sealed with VELCRO® strips or other types of closures (e.g., zippers) as desired.

Figure 5C:
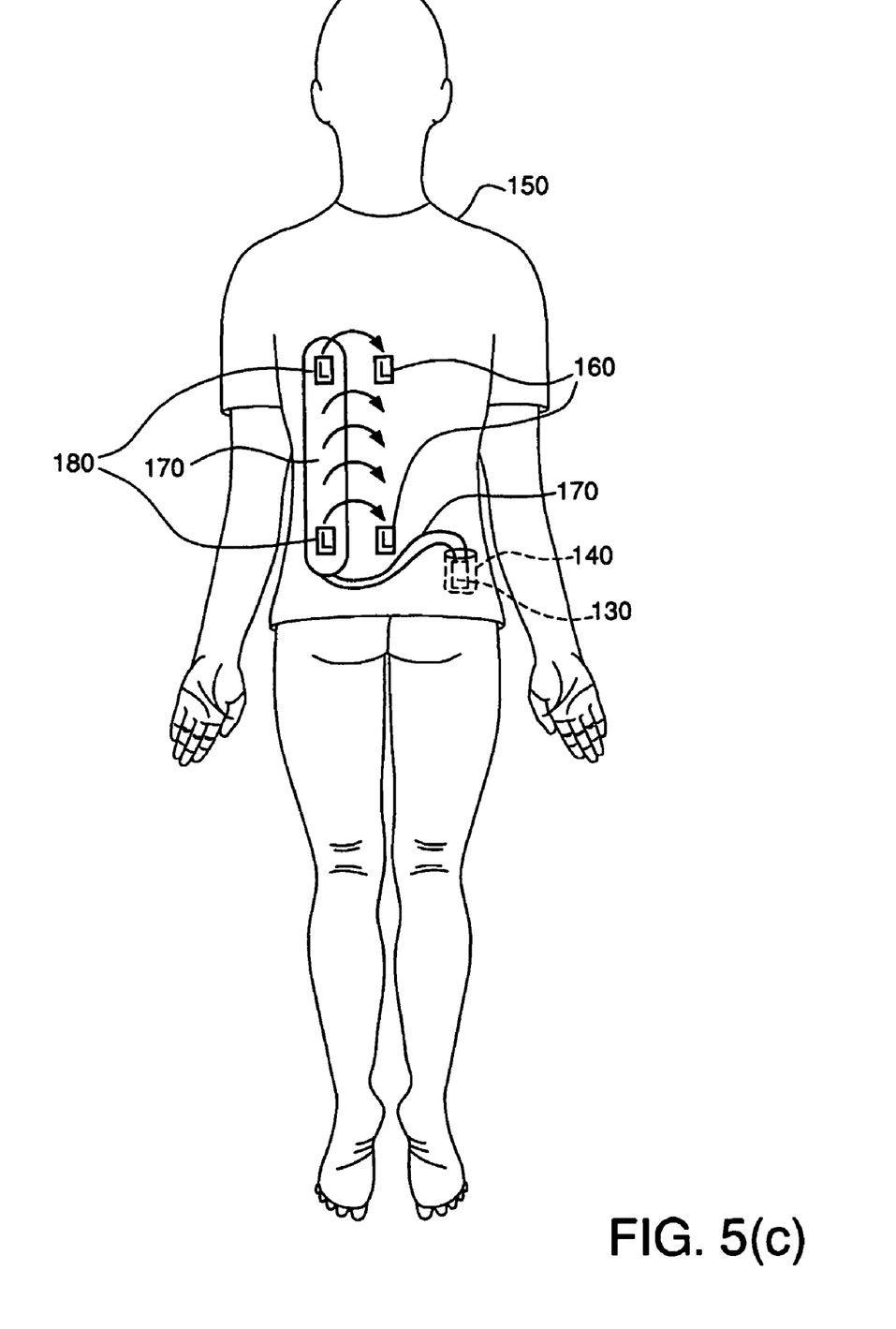
FIG. 5(c) illustrates an undershirt modified to include VELCRO® strips at the desired treatment location of the patient's spine for receiving the conductive flexible coil of FIG. 1.

FIG. 5(c) illustrates an undershirt 150 modified to include VELCRO® loops (L) 160 spaced along the spine at desired distances and attached to undershirt 150 in a conventional manner as shown. Conductive flexible coil 170 of the type shown in FIG. 1 is mounted on a substrate or fabric or inserted into a pouch with VELCRO® loops (L) 180 and is centered over the treatment area of the patient's spine by connecting counterpart VELCRO® localizers 160 and 180. A connector 190 connects the coil 170 to power pack 130 that is preferably worn on a belt around the patient's waist or placed in a pouch 140 of the undershirt 150 as shown. The pouches may be sealed with VELCRO® strips or other types of closures (e.g., zippers) as desired.

The garment for the hip will look like form fitting panties or men's shorts with the conductive, flexible coil of FIG. 2 either woven into the garment over one or both hips, mounted on a separate piece of fabric or substrate for insertion into a pouch in the panties or shorts so as to be centered over one or both hips, or the coil 40 may be attached to VELCRO® strips at the desired location.

Figure 6A:
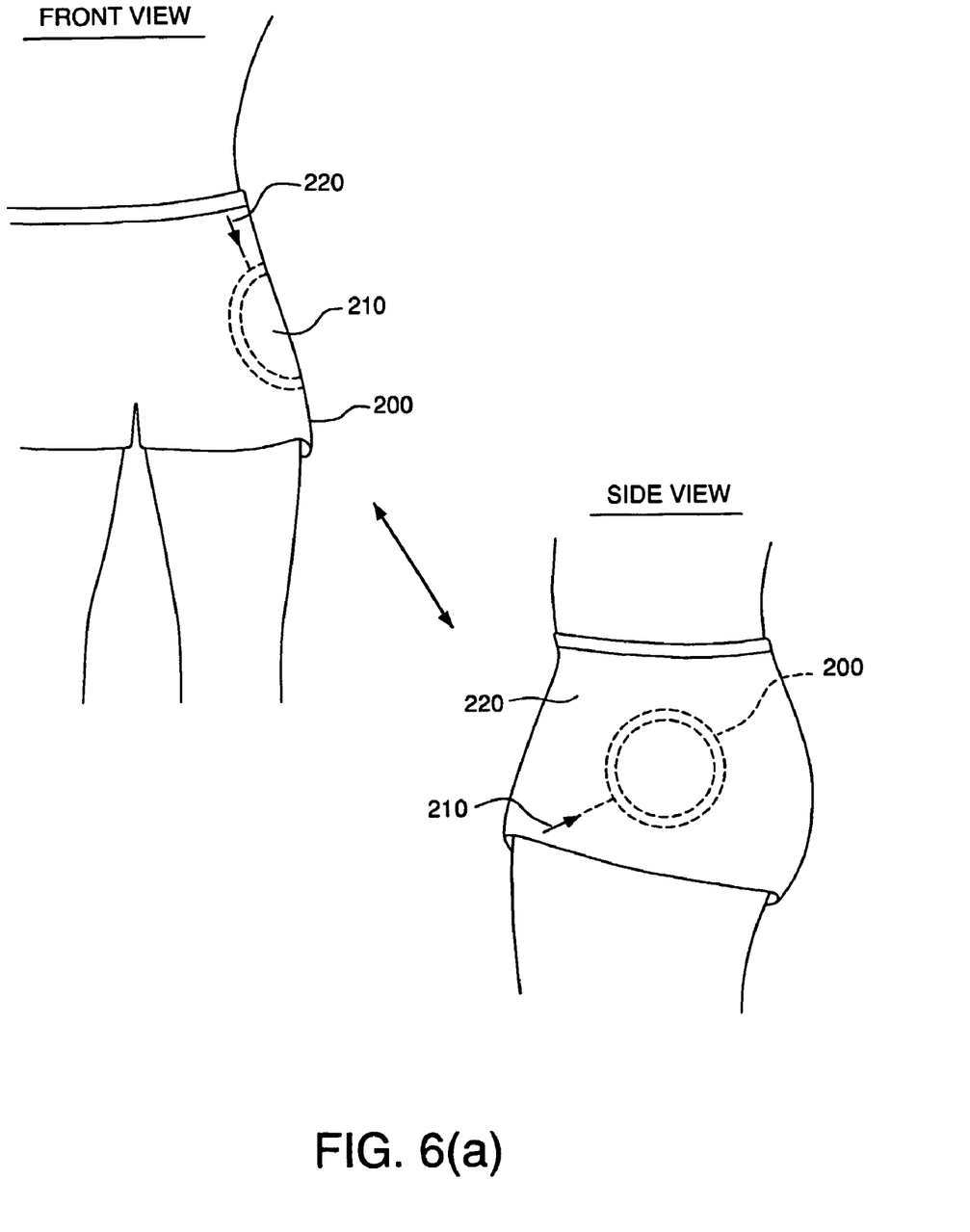
FIG. 6(a) illustrates women's panties modified to include the conductive flexible coil of FIG. 2 woven into the panties for placement over one or both of the patient's hips.

FIG. 6(a) illustrates panties or shorts 200 modified to include a flexible conductive coil 210 of the type shown in FIG. 2 woven into the panties or shorts 200 for placement and retention at a location centered over the treatment area of the patient's hip(s). A connector 220 with soft, flexible leads connects the coil 210 to a power pack (not shown) preferably worn on a belt around the patient's waist or in a pouch of the panties or shorts 200.

Figure 6B:
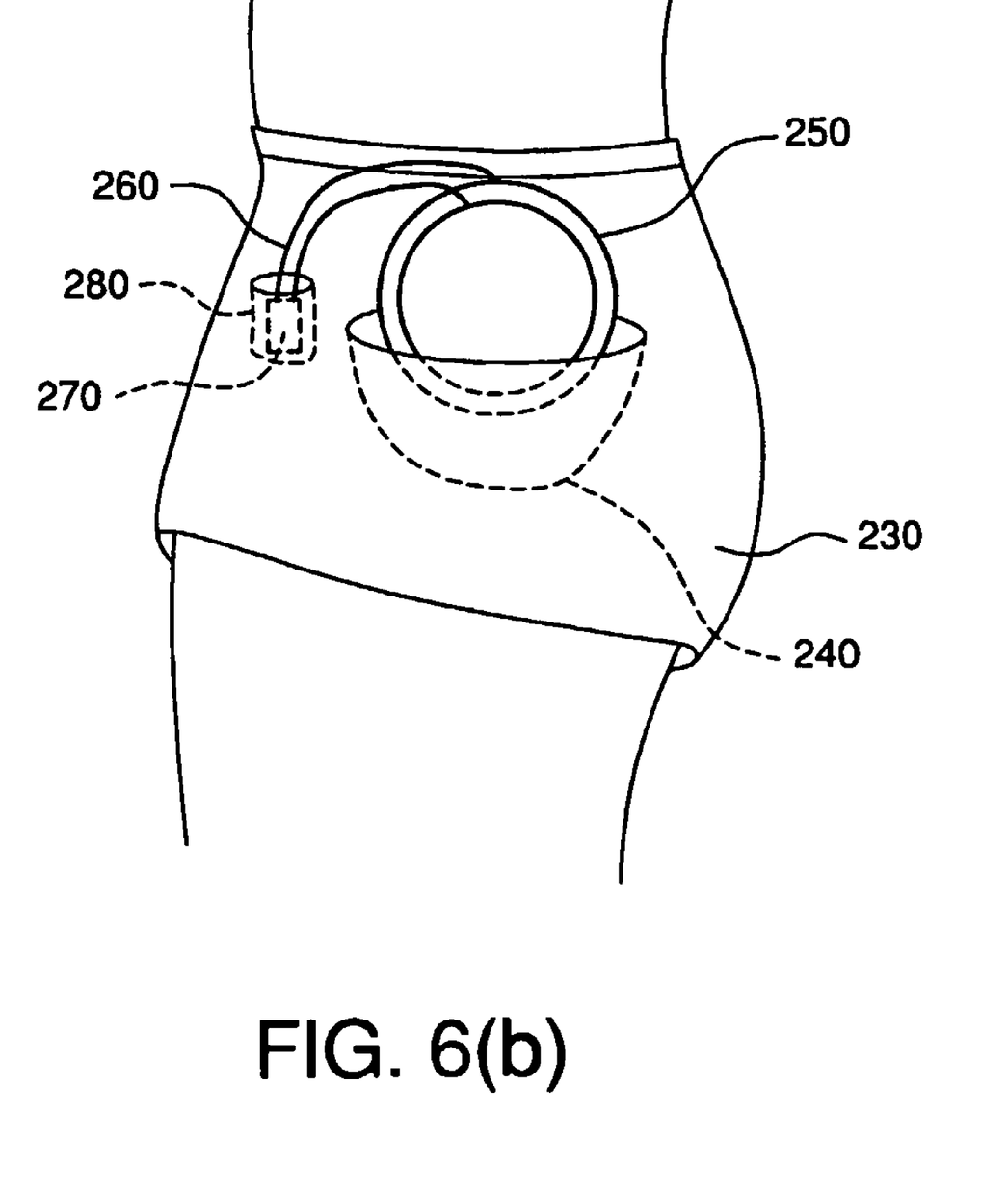
FIG. 6(b) illustrates women's panties modified to include a pouch for receiving the conductive flexible coil of FIG. 2 mounted on a separate piece of fabric or substrate for insertion into the pouch for placement over one or both of the patient's hips.

FIG. 6(b) illustrates panties or shorts 230 modified to include a pouch 240 for receiving the conductive flexible coil 250 of the type shown in FIG. 2 except that the coil 250 is mounted on a substrate or separate piece of fabric to facilitate insertion into the pouch 240. The pouch 240 is centered over the treatment area of the patient's hip. A connector 260 connects the coil 250 to power pack 270 that is preferably worn on a belt around the patient's waist or placed in a pouch 280 of the panties or shorts 230 as shown. The pouches may be sealed with VELCRO® strips or other types of closures (e.g., zippers) as desired.

Figure 6C:
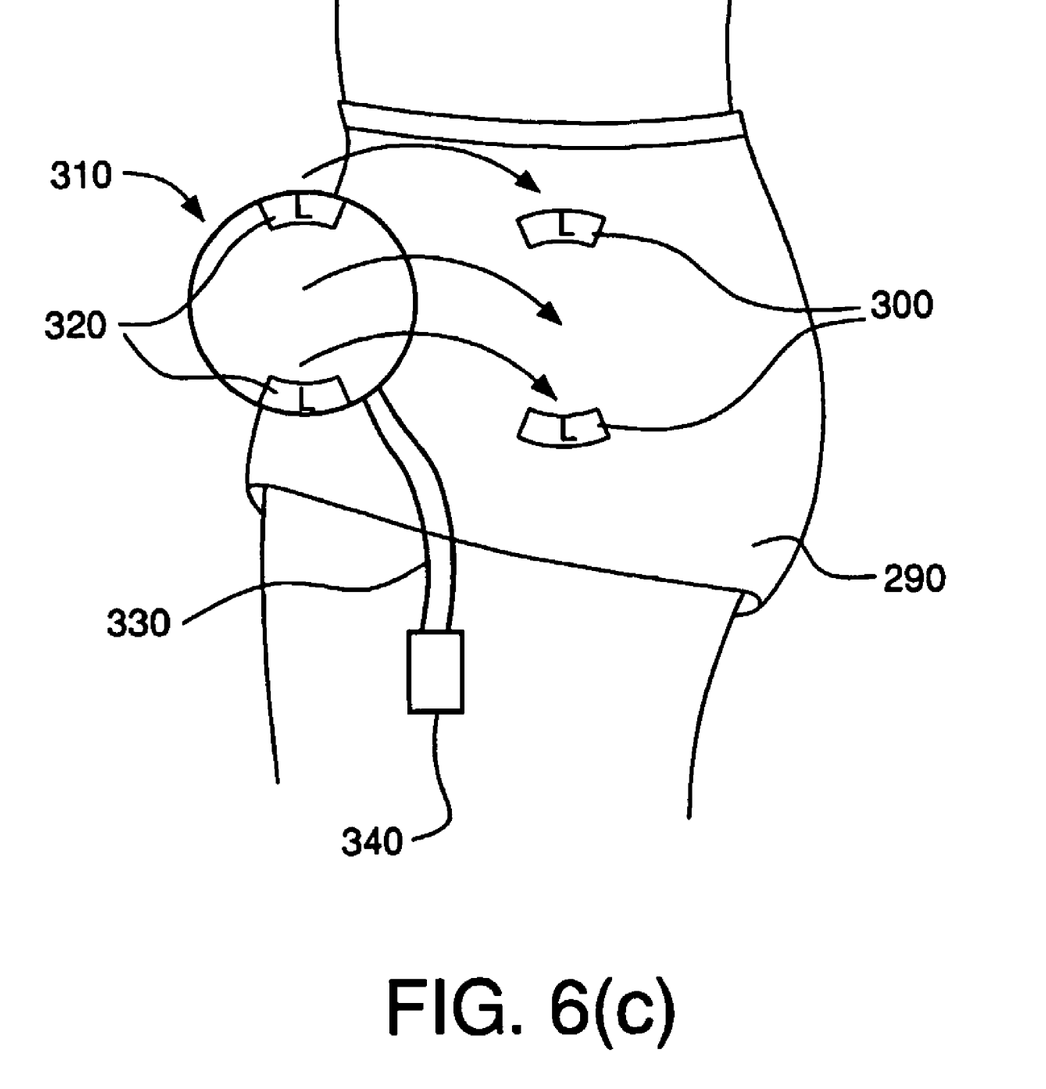
FIG. 6(c) illustrates women's panties modified to include VELCRO® strips for receiving the conductive flexible coil of FIG. 2 over the patient's hips.

FIG. 6(c) illustrates panties or shorts 290 modified to include VELCRO® loops (L) 300 spaced along the hip(s) at desired distances and attached to panties or shorts 290 in a conventional manner as shown. Conductive flexible coil 310 of the type shown in FIG. 2 is mounted on a substrate or fabric or inserted into a pouch with VELCRO® loops (L) 320 and is centered over the treatment area of the patient's hip by connecting counterpart VELCRO® localizers 300 and 320. A connector 330 connects the coil 310 to power pack 340 that is preferably worn on a belt around the patient's waist or placed in a pouch 280 (FIG. 6(b)) of the panties or shorts 290. The pouches may be sealed with VELCRO® strips or other types of closures (e.g., zippers) as desired.

Although exemplary implementations of the invention have been described in detail above, those skilled in the art will readily appreciate that many additional minor modifications are possible in the exemplary embodiments without materially departing from the novel teachings and advantages of the invention. For example, other electric signals with different characteristics and different characteristic frequencies (e.g., in the range of 30 kHz to 250 kHz) may be applied to the coils for providing treatment in accordance with the invention. Any such minor modifications are intended to be included within the scope of this invention as defined by the following exemplary claims.

We claim:

1. A method of preventing and/or treating osteoporosis, bone fracture, and/or bone fusion in a patient, comprising the steps of:

incorporating at least one conductive coil N turns, where N>1, into an article of clothing adapted to be worn on the patient's torso adjacent the patient's skin, whereby the article of clothing, when worn, causes the coil to be located over a treatment area of the patient; and applying an electrical signal to the coil effective to produce a magnetic flux that penetrates the treatment area so as to produce an electric field in the treatment area effective to treat osteoporosis, fracture and/or fusion of bones of the treatment area.

2. The method of claim 1, comprising the additional step of providing a portable power device that creates said electrical signal for application to the coil, said portable power device being sufficiently small and light to be carried on the patient's body when the article of clothing is being worn.

3. The method of claim 2, wherein the portable power device is adapted to provide to said coil a 60 kHz sinusoidal electrical current with a sine wave amplitude of 100 mA.

4. The method of claim 1, wherein the article of clothing is an undershirt and the coil is configured in a racetrack design having a long axis along the treatment area of the patient's spine when incorporated into the undershirt.

5. The method of claim 4, wherein the coil is woven into the undershirt.

6. The method of claim 4, wherein the coil is placed in a pouch in the undershirt.

7. The method of claim 4, wherein the coil is attached to the undershirt by VELCRO®.

8. The method of claim 1, wherein the article of clothing is underpants and the coil is generally circular in shape and centered over the patient's hip when incorporated into the underpants.

9. The method of claim 8, wherein the coil is woven into the underpants.

10. The method of claim 8, wherein the coil is placed in a pouch in the underpants.

11. The method of claim 8, wherein the coil is attached to the underpants by VELCRO®.

12. The method of claim 8, wherein the underpants are adapted to accept a generally circular-shaped coil over both hips of the patient.

13. A system for preventing and/or treating osteoporosis, bone fracture, and/or bone fusion in a patient, comprising:
an article of clothing adapted to be worn on the patient's torso adjacent the patient's skin, said article of clothing including at least one conductive coil N turns, where N>1, incorporated therein such that, when worn, the coil is located over a treatment area of the patient; and
a portable signal generating device that generates an electrical signal for application to the coil to produce a magnetic flux that penetrates the treatment area so as to produce an electric field in the bones of the treatment area effective to treat osteoporosis, bone fracture and/or bone fusion of bones of the treatment area.

14. The system of claim 13, wherein the portable signal generating device comprises a rechargeable battery and is sufficiently small and light to be carried on the patient's body when the article of clothing is being worn.

15. The system of claim 13, wherein the portable signal generating device is adapted to provide to said coil a sinusoidal electrical current in a frequency range of 30 kHz to 250 kHz with a sine wave amplitude of 100 mA.

16. The system of claim 15, wherein the portable signal generating device is adapted to provide to said coil a 60 kHz sinusoidal electric current.

17. The system of claim 13, wherein the article of clothing is an undershirt and the coil is configured in a racetrack design having a long axis along the treatment area of the patient's spine when incorporated into the undershirt.

18. The system of claim 17, wherein the coil is woven into the undershirt.

19. The system of claim 17, wherein the undershirt includes a pouch for accepting the coil.

20. The system of claim 17, wherein the undershirt includes VELCRO® strips for accepting the coil.

21. The system of claim 13, wherein the article of clothing is underpants and the coil is generally circular in shape and centered over the patient's hip when incorporated into the underpants.

22. The system of claim 21, wherein the coil is woven into the underpants.

23. The system of claim 21, wherein the underpants include a pouch for accepting the coil.

24. The system of claim 21, wherein the coil is attached to the underpants by VELCRO®.

25. The system of claim 21, wherein the underpants are adapted to accept a generally circular-shaped coil over both hips of the patient.

* * * * *

UNITED STATES PATENT AND TRADEMARK OFFICE
CERTIFICATE OF CORRECTION

PATENT NO. : 7,158,835 B2 Page 1 of 1
APPLICATION NO. : 10/499191
DATED : January 2, 2007
INVENTOR(S) : Carl T. Brighton et al.

It is certified that error appears in the above-identified patent and that said Letters Patent is hereby corrected as shown below:

Title Page,
Item (57), ABSTRACT:
Line 6, delete "the" and insert -- that --.

Title Page,
Item (56) References Cited
OTHER PUBLICATIONS:
Page 2, "Grodzinky, A.J.," reference, delete "Grodzinky," and insert
-- Grodzinsky, --.
Page 2, "Wang, W. et al.," reference, delete "constributes" and insert
-- contributes --.

Column 8,
Line 60, delete "coil N turns," and insert -- coil of N turns, --.

Column 9,
Line 39, delete "coil N turns," and insert -- coil of N turns, --.

Signed and Sealed this

Seventh Day of October, 2008

JON W. DUDAS
*Director of the United States Patent and Trademark Office*